United States Patent [19]

Nettleton, Jr. et al.

[11] Patent Number: 4,487,925

[45] Date of Patent: Dec. 11, 1984

[54] REBECCAMYCIN AND PROCESS FOR ITS PREPARATION

[75] Inventors: Donald E. Nettleton, Jr., Jordan; James A. Bush, Fayetteville; William T. Bradner, Manlius; Terrence W. Doyle, Fayetteville, all of N.Y.

[73] Assignee: Bristol-Myers Company, New York, N.Y.

[21] Appl. No.: 461,817

[22] Filed: Jan. 28, 1983

[51] Int. Cl.³ .......................................... C07H 17/00
[52] U.S. Cl. ..................................... 536/24; 424/180
[58] Field of Search .......................................... 536/24

[56] References Cited

PUBLICATIONS

Furwaki et al., Journ. Chem. Comm. (J.C.S.), 1978, pp. 800–801.
Omura et al., Journ. Antibiotics 30 (4); 275–282 (1977).
Steglich et al., Angew. Chemie 19 (6), pp. 459–460 (1980).

*Primary Examiner*—Ethel G. Love
*Attorney, Agent, or Firm*—David M. Morse

[57] ABSTRACT

A novel antitumor agent designated herein as rebeccamycin is produced by fermentation of *Nocardia aerocolonigenes* (ATCC 39243). Rebeccamycin and its 5'-N-methyl and 5',2",3",6"-tetraacetate derivatives exhibit activity against experimental animal tumor systems.

3 Claims, No Drawings

REBECCAMYCIN AND PROCESS FOR ITS PREPARATION

BACKGROUND OF THE INVENTION

1. Field of the Invention

This invention relates to novel antitumor agents and to their production and recovery.

2. Description of the Prior Art

The novel antitumor agents of the present invention are believed to represent a unique chemical structure.

Somewhat similar in structure to the antitumor agents of the present invention is the antitumor agent, staurosporine (also called AM-2282), obtained from fermentation of *Streptomyces staurosporeus*. Staurosporine is described in *J.C.S. Chem. Comm.*, 1978, pg. 800–801 and in *J. Antibiotics* 30(4): 275–282 (1977).

*Angew Chem. Int. Ed. Engl.* 19(6): 459–460 (1980) discloses several indole pigments obtained from the fruiting bodies of the slime mold *Arcyria denudata* which are structurally related to staurosporine. Certain of the pigments exhibit activity against *Bacillus brevis* and *B. subtilis*.

SUMMARY OF THE INVENTION

This invention relates to a novel antitumor agent designated herein as rebeccamycin and to its 5′-N-methyl and 5′,2″,3″,6″-tetraacetate derivatives. Rebeccamycin is obtained by cultivating a rebeccamycin-producing strain of *Nocardia aerocolonigenes*, preferably *Nocardia aerocolonigenes* strain C38,383-RK2 (ATCC 39243) or a mutant thereof, in an aqueous nutrient medium under submerged aerobic conditions until a substantial amount of rebeccamycin is produced by said microorganism in said culture medium and, optionally, recovering the rebeccamycin from the culture medium. The tetraacetate derivative is obtained by acetylation of rebeccamycin and the 5′-N-methyl derivative is obtained by methylation of rebeccamycin, e.g. with methyl iodide and potassium carbonate in an inert solvent such as acetone.

Rebeccamycin and its tetraacetate and 5′-N-methyl derivatives exhibit activity against experimental animal tumor systems, e.g. P-388 leukemia in mice.

There is thus provided by the present invention rebeccamycin having the formula

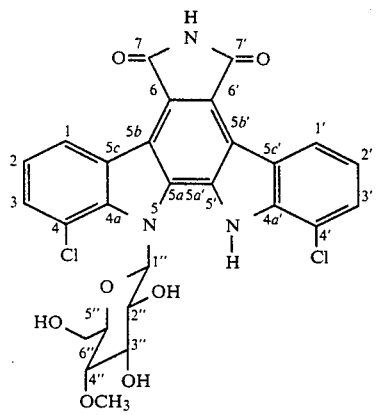

rebeccamycin-5′,2″,3″,6″-tetraacetate having the formula

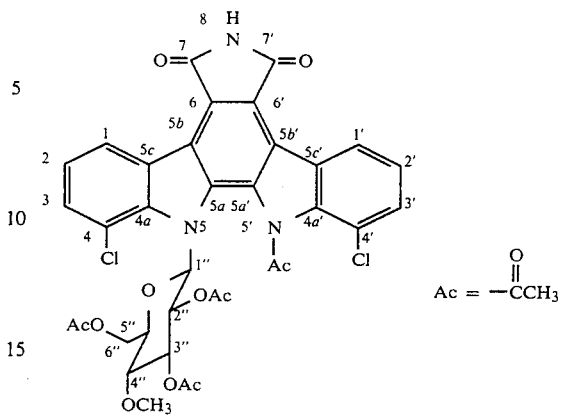

and 5′-N-methylrebeccamycin having the formula

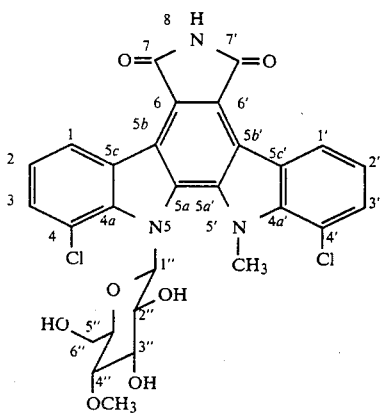

DETAILED DESCRIPTION

The rebeccamycin antitumor agent of the present invention is produced by fermentation of a rebeccamycin-producing strain of *Nocardia aerocolonigenes*.

An especially preferred rebeccamycin-producing strain has been isolated from a soil sample collected in Panama and designated by the inventors as strain C38,383-RK2. Cultures of this strain have been deposited in the American Type Culture Collection, Rockville, Maryland, and added to their permanent collection of microorganisms as ATCC 39243.

The results of taxonomic studies performed on strain C38,383-RK2 indicate that the strain is classified as an atypical species of the genus Nocardia. Based on the characteristics indicated below, strain C38,383-RK2 is believed to belong to the species group of *Nocardia aerocolonigenes*.

Strain C38,383-RK2 has the following properties:

Morphology

Strain C38,383-RK2 forms unicellular filamentous cells which develop into substrate and aerial mycelia. Both mycelia are long, well branched and not fragmented into short filaments (0.5 μm in width). Arthrospores are born in the whole of aerial mycelium. These spores are arranged with intercalation of empty hyphae, or formed as a continuous chain. Like the sporulation of *Nocardiopsis dassonvillei*, (*Intl. J. Syst. Bacteriol.* 26: 487–493, 1976) the aerial hyphae of strain C38,383 are divided into long segments which subsequently subdivide into spores of irregular size. The chains of intercalary or continuous spores are straight or flexuous in shape. Extremely long spore-chains which contain 50 to 100 spores in a chain are formed along with short or moderate length of chains. The spores are cylindrical in shape, 0.5~0.7×0.7~5 μm in size, and have a smooth surface.

Sclerotia are formed on the aerial mycelium, but sporangia, motile spores and whorls are not observed.

Cultural Characteristics

Strain C38,383 is an obligately aerobic actinomycete, and grows well in most agar media. The aerial mycelium is formed abundantly on Czapek's sucrose-nitrate agar, ISP Medium Nos. 2,4,5 and 7, nutrient agar and Bennett's agar, but poorly on glucose-asparagine agar and ISP Medium Nos. 3 and 6. The color of aerial mycelium is white, yellowish white or pale yellow. A yellowish pigment is formed in the substrate mycelium, which diffuses slightly into agar medium. This pigment is not a pH-indicator. Melanoid pigment is not produced. The cultural characteristics are shown in Table 1.

Physiological Characteristics

The optimal growth temperature for strain C38,383 ranges from 28° C. to 37° C., and moderate growth is seen at 20° C. and 41° C. No growth is observed at 7° C. and 45° C. Gelatin and starch are decomposed. Tyrosinase reaction is negative. The growth is inhibited in the presence of 8% NaCl, but not by lysozyme at 0.01%. Strain C38,383 utilizes most sugars for growth. The physiological characteristics and utilization of carbohydrates are shown in Tables 2 and 3, respectively.

Cell Wall Amino Acid and Whole Cell Sugar Components

The amino acid composition in the cell wall was examined according to the methods described by Becker et al. (*Appl. Microbial.* 13: 236–243, 1965) and Yamaguchi (*J. Bacteriol.* 89: 441–453, 1965), and the sugar component in the whole cell hydrolyzate was identified according to the procedures outlined by Lechevalier and Lechevalier in *Biology of the Actinomycetes and Related Organisms* 11: 78–92, 1976. The cell wall of strain C38,383 contains meso-diaminopimelic acid but lacks glycine. Whole cell hydrolyzate shows the presence of glucose, galactose, mannose and rhamnose. The abovementioned cell wall composition and whole cell sugar components indicate that the strain C38,383 is an actinomycete species of cell wall type IIIC.

Taxonomy

Strain C38,383 was compared with eight genera of order Actinomycetales, including Nocardia, Micropolyspora, Microtetraspora, Nocardiopsis, Saccharopolyspora, Pseudonocardia, Actinomadura and Streptoalloteichus, all of which produce spore-chains on the aerial mycelium and contain mesodiaminopimelic acid in the cell wall. Among these eight genera, the genus Nocardiopsis is most related to strain C38,383 in the spore-chain and spore morphology, but differs from strain C38,383 in the absence of galactose and mannose in the whole cell hydrolyzate.

Gordon et al. (*J. Gen. Microbiol.* 109: 69–78, 1978) characterized 14 taxa of nocardiae based on the physiological properties and the chemical composition in whole cell hydrolyzate. Strain C38,383 was most similar to *Nocardia aerocolonigenes* in the amino acid and sugar composition in whole cell hydrolyzate. Therefore, strain C38,383 was compared with the diagnostic physiological properties of *N. aerocolonigenes*. As shown in Table 4, strain C38,383 was found to be closely related to *N. aerocolonigenes* but significantly different from *Nocardia* (Nocardiopsis) *dassonvillei*. However, all 14 strains of *N. aerocolonigenes* lack or lose the abilities to form spores and aerial mycelium. Thus, strain C38,383 is considered to be a sporogenic species in the taxon of *Nocardia aerocolonigenes*.

Strain C38,383 was also found to lose its ability to form aerial mycelium and spores. After five successive transfers, 70% of single isolates lost these abilities. Such property of strain C38,383 seems to be similar to the reported variation of *Nocardia aerocolonigenes* in the formation of spores and aerial mycelium.

TABLE 1

| Cultural Characteristics of Strain No. C38,383* | | |
|---|---|---|
| Tryptone-yeast extract broth (ISP No. 1) | G**: | moderate; floccose, pale yellow pellets |
| | D: | none |
| Sucrose-nitrate agar (Czapek's agar) | G: | abundant |
| | R: | strong yellow (84)*** to vivid yellow (82) |
| | A: | moderate, yellowish white (92) to pale yellow (89) |
| | D: | dark grayish yellow (91) to light olive brown (94) |
| Glucose-asparagine agar | G: | poor |
| | R: | white (263) |
| | A: | scant, yellowish white (92) to pale yellow (89) |
| | D: | none |
| Glycerol-asparagine agar (ISP No. 5) | G: | abundant |
| | R: | brilliant yellow (83) to strong yellow (84) |
| | A: | abundant, pale yellow (89) to light yellow (86) |
| | D: | yellow gray (93) to grayish yellow (90) |
| Inorganic salts-starch agar (ISP No. 4) | G: | abundant |
| | R: | pale yellow (89) to strong yellow (84) |
| | A: | abundant, white (263) to yellowish white (92) |
| | D: | none |
| Tyrosine agar (ISP No. 7) | G: | abundant |
| | R: | brilliant yellow (83) to strong yellow (84) |
| | A: | moderate, pale yellow (89) to light yellow (86) |
| | D: | pale yellow (89) |
| Nutrient agar | G: | abundant |
| | R: | yellowish white (92) to pale yellow (89) |
| | A: | abundant, white (263) |
| | D: | none |
| Yeast extract-malt extract agar (ISP No. 2) | G: | abundant |
| | R: | brilliant orange yellow (67) to strong orange yellow (68) |
| | A: | abundant, yellowish white (92) to pale yellow (89) |
| | D: | dark orange yellow (72) to moderate yellowish brown (77) |
| Oat meal agar (ISP No. 3) | G: | moderate |
| | R: | light yellow (86) to brilliant yellow (83) |
| | A: | scant, yellowish white (92) to pale yellow (89) |
| | D: | none |
| Bennett's agar | G: | abundant |
| | R: | brilliant yellow (83) to strong yellow (84) |

TABLE 1-continued

Cultural Characteristics of Strain No. C38,383*

| | | |
|---|---|---|
| Peptone-yeast extract-iron agar (ISP No. 6) | A: | abundant, yellowish white (92) to pale yellow |
| | D: | vivid yellow (82) |
| | G: | moderate |
| | R: | pale yellow (89) to light yellow (86) |
| | A: | poor, white (263) to yellowish white (92) |
| | D: | none |

*observed after incubation at 28° C. for 3 weeks
**Abbreviation: G = growth; R = reverse color; A = aerial mycelium; D = diffusible pigment
***Color and number in parenthesis follow the color standard in Kelly, K.L. & D.B. Judd: ISCC-NBS color-name charts illustrated with CentroidColors. US Dept. of Comm. Cir. 553, Washington, D.C., No., 1975".

TABLE 2

Physiological Characteristics of Strain No. C38,383

| Test | Response | Method or Medium used |
|---|---|---|
| Range of temperature for growth | Maximal growth at 28° C. to 37° C. Moderate growth at 20° C. and 41° C. No growth at 7° C. and 45° C. | Bennett's agar |
| Gelatin liquefaction | Liquefied | 1% malt extract, 0.4% yeast extract, 0.4% glucose, 20% gelatin. |
| Starch hydrolysis | Hydrolyzed | Starch agar plate |
| Reactions in skimmed milk | Not coagulated and completely peptonized | Difco skimmed milk |
| Formation of melanoid pigment | negative | Tyrosine agar, peptone-yeast extract-iron agar, and tryptone-yeast extract broth |
| Tyrosinase reaction | Negative | Arai's method* |
| Nitrate reduction | Positive | Czapek's sucrose-nitrate broth |
| | Positive | 0.5% yeast extract, 1% glucose, 0.5% KNO$_3$, 0.1% CaCO$_3$. |
| Acid tolerance | Growth at pH 5.0. No growth at pH 4.5. | Yeast extract-malt extract agar |
| NaCl tolerance | Growth at 7% NaCl or less. No growth at 8% NaCl. | Basal medium: 1% yeast extract, 2% soluble starch, 1.5% agar. |
| Lysozyme tolerance | Tolerant. Growth at 0.01% lysozyme. | Trypticase soy broth plus 1.5% agar. |

*Arai, T. and Y. Mikami: Chromogenicity of Streptomyces. Appl. Microbiol. 23: 402–406, 1972.

TABLE 3

Carbohydrate Utilization of Strain No. C38,383

| | |
|---|---|
| Glycerol | + |
| D(−)-Arabinose | + |
| L(+)-Arabinose | + |
| D-Xylose | + |
| D-Ribose | + |
| L-Rhamnose | + |
| D-Glucose | + |
| D-Galactose | + |
| D-Fructose | + |
| D-Mannose | + |
| L(−)-Sorbose | − |
| Sucrose | + |
| Lactose | + |
| Melibiose | + |
| Trehalose | + |
| Raffinose | + |
| D(+)-Melezitose | − |
| Soluble starch | + |
| Cellulose | + |
| Dulcitol | − |
| Inositol | + |
| D-Mannitol | + |
| D-Sorbitol | − |
| Salicin | + | observed after incubation at 37° C. for 3 weeks
Basal medium: Pridham-Gottlieb's inorganic medium
Abbreviation:
+: positive utilization.
−: negative utilization

TABLE 4

Comparison of diagnostic physiological properties among strain C38,383, *Nocardia aerocolonigenes* and *Nocardiopsis dassonvillei*

| | Strain C38,383 | *Nocardia* *aerocolonigenes* (14)** | *Nocardiopsis* *dassonvillei* (31)** |
|---|---|---|---|
| Decomposition of: | | | |
| Adenine | − | − | + |
| Casein | + | + | + |
| Hypoxanthine | + | + | + |
| Tyrosine | + | + | + |
| Urea | − | + | − |
| Xanthine | − | − | + |
| Resistance to: | | | |
| Lysozyme | + | + | − |
| Rifampin | − | − | − |
| Hydrolysis of: | | | |
| Aesculin | + | + | − |
| Hippurate | − | V | + |
| Starch | + | + | + |
| Acid from: | | | |
| Inositol | + | + | − |
| Lactose | + | + | − |
| Melibiose | + | + | − |
| Raffinose | + | V | − |
| Utilization of: | | | |
| Benzoate | − | − | − |
| Citrate | + | + | + |
| Mucate | − | − | − |
| Succinate | + | + | + |
| Tartrate | − | − | − |
| Nitrite from nitrate | + | V | + |
| Survival at 50° C., 8h | − | V | + |

+: positive. −: negative. V: 15 to 84% of the strains positive
*Data of Gordon et al. (J. Gen. Microbiol. 109:69–78, 1978)
**No. of strains examined It is to be understood that the present invention is not limited to use of the particular preferred strain C38,383-RK2 described above or to organisms fully answering the above descriptions. It is especially intended to include other rebeccamycin-producing strains or mutants of the said organism which can be produced by conventional means such as x-radiation, ultraviolet radiation, treatment with nitrogen mustards, phage exposure, and the like.

PREPARATION OF REBECCAMYCIN

Rebeccamycin may be produced by cultivating a rebeccamycin-producing strain of *Nocardia aerocolonigenes*, preferably a strain having the characteristics of *Nocardia aerocolonigenes* strain C38,383-RK2 (ATCC 39243) or a mutant thereof, under submerged aerobic conditions in an aqueous nutrient medium. The organism is grown in a nutrient medium containing an assimilable carbon source, for example, sucrose, lactose, glucose, rhamnose, fructose, mannose, melibiose, glycerol or soluble starch. The nutrient medium should also contain an assimilable nitrogen source such as fish meal, peptone, soybean flour, peanut meal, cottonseed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of rebeccamycin can be effected at any temperature conducive to satisfactory growth of the organism, e.g. 20°–41° C., and is conveniently carried out at a temperature of about 27° C.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of rebeccamycin. The medium in which the vegetative inoculum is produced can be the same as, or different from, that utilized in the tank as long as it is such that a good growth of the producing organism is obtained.

In general, optimum production of rebeccamycin is achieved after incubation periods of about seven days.

Rebeccamycin is the major product of the fermentation and is found only in the mycelium. Recovery from the mycelium may be effected by extraction with an organic solvent such as tetrahydrofuran or acetone. After reduction of the extract volume in vacuo to an aqueous concentrate, rebeccamycin precipitates as a fine solid. A wash with diethyl ether, methyl tert-butyl ether or other relatively non-polar solvent is then carried out to remove oils which make subsequent filtration difficult. The crude rebeccamycin concentrate floats at the interface and is easily isolated by filtration. Purified crystalline rebeccamycin may be obtained by recrystallization of the crude product from a suitable organic solvent mixture such as tetrahydrofuran-methanol.

PHYSICOCHEMICAL PROPERTIES REBECCAMYCIN

The physicochemical properties of purified rebeccamycin are as follows:

Rebeccamycin is a yellow crystalline solid, fluorescing intensely under 254 and 366 nm light, yellow as the solid and green to blue in solutions. It is soluble in tetrahydrofuran and dimethylsulfoxide and slightly soluble in acetone and mixtures of lower alcohols with methylene chloride or chloroform.

Infrared spectrum: The infrared absorption spectrum of rebeccamycin (KBr) shows major bands at the following wave lengths: 3418, 3355, 1752, 1704, 1575, 1465, 1431, 1411, 1379, 1327, 1273, 1213, 1191, 1174, 1144, 1110, 1075, 1048, 970, 799, 788, 757 cm$^{-1}$.

Ultraviolet spectrum: At a concentration of 0.01138 g/l in methanol, rebeccamycin exhibits the following maxima and absorptivities: 238 nm(75.75), shoulder at 256 nm(29.79), 293 nm(55.27), 314 nm(90.51), 362 nm(8.35), 389–391 nm(7.91).

Nuclear magnetic resonance spectra:

a. 100 MHz pmr spectrum: When rebeccamycin was dissolved in dimethylsulfoxide, the spectrum showed the following chemical shifts in ppm and pattern descriptions: 11.37(s, 1H, N5'-H), 10.30(s, 1H, N8-H), 9.27(d, 1H, C1-H), 9.09(d, 1H, C1'-H), 7.74 and 7.69(ds, 2H, C3-H and C3'-H), 7.45(t, 2H, C2-H and C2'-H), 6.97(d, 1H, C1''-H), 5.45(d, 1H, C3''-OH), 5.36(t, 1H, C6''-OH), 5.03(d, 1H, C2''-OH), 3.90(bt, 2H, C6''-CH$_2$), 3.66 (quintet, 1H, C5''-H), 3.56(dt, 1H, C2''-H), 3.53(t, 1H, C4''-H), 3.48(s, 3H, OCH$_3$), 3.45(obscured, 1H, C3''-H).

b. 25 MHz $^{13}$cmr spectrum: When rebeccamycin was dissolved in DMSO d$_6$, the spectrum showed the following observed chemical shifts:

| PPM | Description |
|---|---|
| 170.3 | C7 |
| 170.1 | C7' |
| 137.4 | C4a |
| 137.0 | C4a' |
| 129.7 | C3' |
| 129.5 | C5a and C5a' |
| 126.9 | C3 |
| 124.9 | C5 |
| 123 | C5' |
| 123 | C1 |
| 123.1 | C1' |
| 122.4 | C2 and C6 |
| 121.9 | C2' |
| 120.4 | C6' |
| 119.2 | C4' |
| 117.5 | C4 |
| 116.0 | C5b and C5b' |
| 84.2 | C1'' |
| (80.1) | C3'' |
| (79.0) | C4'' |
| (77.2) | C5'' |
| 72.0 | C2' |
| 60.0 | OCH$_3$ |
| 59.7 | C6'' |

Optical rotation (tetrahydrofuran): $\alpha_D^{21} = +131$; $\alpha_{578}^{21} = +137.4$; $\alpha_{546}^{21} = +166.1$.

Analysis of rebeccamycin in mixtures was accomplished by high performance liquid chromatography (HPLC) on the RCM-100 (Waters Associates, Milford, Mass.) system using a Radial Pack Silica cartridge, 8 mm ID×10 cm, 10μ packing, with a 2% methanol in chloroform solvent system. Retentions observed were k'=2.46–2.60.

PREPARATION OF REBECCAMYCIN DERIVATIVES

Rebeccamycin may be converted to its 5',2'',3'',6''-tetraacetate derivative (formula II above) by acetylation in an inert solvent. For example, rebeccamycin may be reacted with acetic anhydride in a pyridine solvent. The tetraacetate derivative is also found to have antitumor activity in experimental animal tumor systems.

Methylation of rebeccamycin as by treatment with methyl iodide and potassium carbonate in an inert solvent such as acetone gives the 5'-N-methylrebeccamycin derivative which also shows antitumor activity in experimental animal tumor systems.

BIOLOGICAL ACTIVITY OF REBECCAMYCIN AND ITS DERIVATIVES

Rebeccamycin was tested for antitumor activity against the transplanted mouse leukemia P-388 according to procedures of Geran, et al., Cancer Chemother. Rpts. 3: 1–103, 1972. Prolongation of survival of leukemic mice was observed at several dose levels ranging from 8 to 256 mg/kg. Results of the test are shown below. The comparison agent, NSC 38270, is olivomycin A.

TABLE 5
Effect of Rebeccamycin on P-388 Leukemia

| Material | Dose, IP mg/kg/inj | MST Days | MST % T/C | Average weight change, gm day 5 | Survivors day 10 (30) |
|---|---|---|---|---|---|
| NSC 38270 | 0.8 | 11.5 | 144 | −1.1 | 6/6 |
| (Olivomycin A) | 0.4 | 11.0 | 138 | −0.6 | 6/6 |
| Rebeccamycin | 256 | 13.0 | 163 | −0.8 | 6/6 |
| | 128 | 12.0 | 150 | −0.7 | 6/6 |
| | 64 | 10.5 | 131 | −0.2 | 6/6 |
| | 32 | 10.0 | 125 | −1.1 | 6/6 |
| | 16 | 10.0 | 125 | +1.0 | 6/6 |
| | 8 | 10.0 | 125 | +2.2 | 6/6 |
| Control | Saline | 8.0 | — | +1.6 | 10/10 |

Tumor inoculum: $10^6$ ascites cells, ip
Host: $CDF_1$ ♀ mice
Treatment: Day 1 only (except NSC 38270, Days 1, 4 and 7)
Tox: <4/6 mice alive on Day 5
Evaluation: MST = median survival time
Effect: % T/C = (MST treated/MST control) × 100
Criteria: % T/C ≧ 125 considered significant antitumor activity When tested for antimicrobial effects against a number of gram-positive and gram-negative bacteria, rebeccamycin exhibited no significant antimicrobial activity.

THERAPEUTIC USE

As mentioned above, rebeccamycin and its 5′,2″,3″,6″-tetraacetate and 5′-N-methyl derivatives exhibit antitumor activity against mammalian malignant tumors, e.g. P-388 leukemia in mice.

The present invention, therefore, provides a method for therapeutically treating an experimental animal host affected by a malignant tumor, e.g. P-388 leukemia, sensitive to rebeccamycin or its tetraacetate of 5′-N-methyl derivatives which comprises administering to said host an effective tumor-inhibiting dose of rebeccamycin or its tetraacetate of 5′-N-methyl derivative.

In another aspect the present invention provides a pharmaceutical composition which comprises an effective tumor-inhibiting amount of rebeccamycin or its tetraacetate or 5′-N-methyl derivative thereof in combination with an inert pharmaceutically acceptable carrier or diluent. These compositions may be made up in any appropriate pharmaceutical form appropriate for the desired route of administration.

Examples of suitable compositions include solid compositions for oral administration such as tablets, capsules, pills, powders and granules, liquid compositions for oral administration such as solutions, suspensions, syrups and elixers and preparations for parenteral administration such as sterile solutions, suspensions or emulsions. They may also be manufactured in the form of sterile solid compositions which can be dissolved in sterile water, physiological saline or some other sterile injectable medium immediately before use.

It will be appreciated that the actual preferred dosages of the rebeccamycin (or derivative thereof) will vary according to the particular compound being used, the particular composition formulated, the mode of application and the particular situs, host and disease being treated. Many factors that modify the action of the drug will be taken into account by those skilled in the art, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by those skilled in the art using conventional dosage determination tests.

The following examples are provided for illustrative purposes only are not intended to limit the scope of the claimed invention.

EXAMPLE 1

PREPARATION OF REBECCAMYCIN

A. Fermentation

*Nocardia aerocolonigenes* strain C38,383-RK2 (ATCC 39243) was maintained and transferred in test tubes on agar slants of yeast-malt extract agar. This medium consists of 4.0 g glucose, 4.0 g yeast extract, 10 g malt extract and 20 g agar made up to one liter with distilled water. With each transfer the agar slant was incubated for seven days at 27° C. To prepare an inoculum for the production phase, the surface growth from the slant culture was transferred to a 500 ml Erlenmeyer flask containing 100 ml of sterile medium consisting of 30 g glucose, 10 g soy flour, 10 g cottonseed embryo meal and 3 g $CaCO_3$ made up to one liter with distilled water. This vegetative culture was incubated at 27° C. for 48 hours on a Gyrotory tier shaker (Model G53, New Brunswick Scientific Co., Inc.) set at 210 rev/min describing a circle with a 5.1 cm diameter. Four ml of vegetative culture was transferred to a 500 ml Erlenmeyer flask containing 100 ml of sterile production medium consisting of 60 g corn starch, 10 g glucose, 15 g linseed meal, 5.0 g autolyzed yeast, 1.0 g $FeSO_4.7H_2O$, 1.0 g $NH_4H_2PO_4$, 1.0 g $(NH_4)_2SO_4$ and 10 g $CaCO_3$ made up to one liter with distilled water. The production culture was incubated at 27° C. on a shaker such as used for the vegetative culture. The agitation rate was set at 250 rev/min. At 168 hours, rebeccamycin yield according to HPLC analysis was 183 μg/ml.

B. Isolation

The freshly harvested fermentation (8 liters) carried out according to Example 1A was filtered using a diatomaceous earth filter aid (the filter aid was admixed with the broth and also used to form a mat). The filtrate was discarded and the mat extracted with tetrahydrofuran (10 l) containing approximately 0.025% butylated hydroxytoluenes as preservative. The filtrate from this step was concentrated in vacuo until organic solvent was removed to afford a milky aqueous residue containing fine solids and oils. The latter were removed by extraction with diethyl ether or (for larger scale work) with methyl tert-butyl ether, the remaining precipitate forming a mass of yellowish fine particles at the interface. After separation of clear liquor from both phases, the interface was filtered to yield crude rebeccamycin, 1.74 g.

The crude rebeccamycin solid was dissolved in tetrahydrofuran (50 ml) and boiled down to about 20 ml. Hot methanol was added and boiling continued with more alcohol addition until crystallization began. The mixture was then allowed to cool to 8° C. and the solids collected by filtration giving 1.13 g of product as fine yellow needles.

A 750 mg portion of this material was recrystallized from methanol-tetrahydrofuran by redissolution in tetrahydrofuran, filtration through a Millex-SR (Millipore Corp., Bedford, Mass.) 0.5 μm filter and treatment as above to give 363 mg rebeccamycin after drying in vacuo over boiling ethanol for 6 hours.

EXAMPLE 2

Preparation of Rebeccamycin-5',2'',3'',6''-Tetraacetate

Acetic anhydride (1 ml) was added to 10.1 mg rebeccamycin in 2 ml pyridine and the mixture was allowed to stand at ambient temperature (~21° C.) for 17 hours. The mixture was diluted with excess water and extracted with ethyl acetate. The solvent phase was washed with water, dried and concentrated. Crystallization from hexane-ethyl acetate gave the tetraacetate as fine, off-white needles, 9.5 mg.; m.p. 243°–244° C.

Ultraviolet spectrum: At a concentration of 0.01214 g/l methanol, the tetraacetate derivative exhibits the following maxima and absorptivities: 234 nm(58.5), 294 nm(50.2), 315 nm(70.8), 360 nm(8.1), 394 nm(6.3).

Infrared spectrum: The infrared absorption spectrum of the tetraacetate derivative (KBr) shows major bands at the following wave lengths: 3362, 2940, 1782, 1740, 1703, 1541, 1492, 1460, 1427, 1410, 1364, 1327, 1277, 1225, 1202, 1142, 1094, 1047, 790, 758, 590 cm$^{-1}$.

Proton nmr spectra: chemical shifts observed at 10.34(s, 1H, N8-H), 9.18(d, 1H, C1-H), 9.05(d, 1H, C1'-H), 7.84 and 7.80(ds, 2H, C3-H and C3'-H), 7.58(t, 1H, C2-H), 7.52(t, 1H, C2-H), 7.36(d, 1H, C1''-H), 5.60(t, 1H, C3''-H), 5.14(t, 1H, C2''-H), 4.84–4.79(m, H, C6''-H$_2$), 4.75–4.64(m, 2H, C5''-H and C6''-Hb), 3.98(t, 1H, C4''-N), 3.49(s, 3H, OCH$_3$), 2.65(s, 3H, COCH$_3$), 2.10(s, 3H, COCH$_3$), 1.88(s, 3H, COCH$_3$), and 1.04 (s, 3H, 2''-COCH$_3$) ppm.

Anal. Calc'd for C$_{35}$H$_{29}$Cl$_2$N$_3$O$_{11}$: C, 56.92; H, 3.96; N, 5.69; Cl, 9.60. Found: C, 56.65; H, 4.11; N, 5.56; Cl, 9.47.

EXAMPLE 3

Preparation of 5'-N-Methylrebeccamycin

Rebeccamycin (50 mg) and 4g of anhydrous potassium carbonate were suspended in 25 ml acetone, the supernatant liquor becoming deep orange in color. After the addition of 4.0 ml methyl iodide, the mixture was brought to a boil and heated at reflux for about 90 minutes. After cooling to ambient temperature, the reaction mixture was filtered to give a heterogeneous mixture of unreacted carbonate and a pasty yellow material. This was taken up in water and adjusted to pH 5.5 with careful addition of glacial acetic acid, affording a yellow precipitate which was very slightly soluble in ethyl acetate. The precipitate was collected by filtration on inert filter aid, and the dried mat thoroughly leached in tetrahydrofuran. Crystallization from tetrahydrofuran-methanol gave 5'-N-methylrebeccamycin, 21.5 mg.

Evaporation of the reaction mixture filtrate gave a yellow residue which, upon dissolution in tetrahydrofuran, filtration to remove residues of carbonate and crystallization as described above gave additional 5'-N-methylrebeccamycin, m.p. 386°–387° C. (decomp).

Ultraviolet spectrum: At a concentration of 0.01251 g/l methanol, the 5'-N-methylrebeccamycin derivative exhibits the following maxima and absorptivities: 239 nm (72.1), 292 nm (68.7), 316 nm (73.2), 362 nm (shoulder 9.2), 394 nm (7.4).

Infrared spectrum: The infrared absorption spectrum of the 5'-N-methyl derivative (KBr) shows major bands at the following wave lengths: 3345 (broad), 1760, 1708, 1576, 1565, 1464, 1410, 1384, 1325, 1272, 1226, 1198, 1140, 1113, 1071, 1050, 790, 768, 750, 727 cm$^{-1}$.

Proton nmr spectra: chemical shifts observed at 10.67(s, 1H, N8-H), 9.30(d, 1H, C1-H), 9.13(d, 1H, C1'-H), 7.75(d, 1H) and 7.71(d, 1H), (C3 and C3'Hs), 7.46(overlapping doublet appears as a triplet, 2H, C2 and C2'Hs), 6.96(d, 1H, C1''-H), 5.43(d, 1H, C3''-OH), 5.32(t, 1H, C6''-OH), 5.04(d, 1H, C2''-OH), 5.04(s, 3H, N-CH$_3$), 3.98(bt, 2H, C6''-CH$_2$), 3.85(m, 1H, C5''-H), 3.69(m, 1H, C2'-H), 3.66(t, 1H, C4'-H), 3.59(s, 3H, OCH$_3$), 3.58(m, observed, 1H, C3''-H).

Anal. Calc'd for C$_{28}$H$_{23}$Cl$_2$N$_3$O$_7$.½H$_2$O: C, 57.33; H, 4.32; N, 6.92; Cl, 11.67. Found: C, 57.50; H, 4.32; N,

We claim:

1. The compound rebeccamycin having the formula

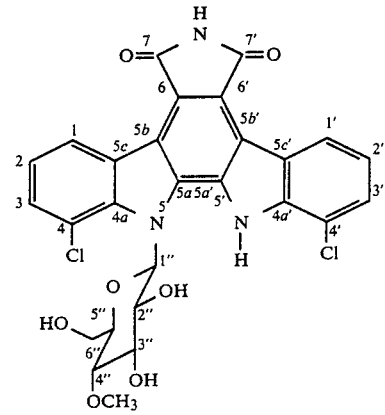

I

2. The compound rebeccamycin 5',2'',3'',6''-tetraacetate having the formula

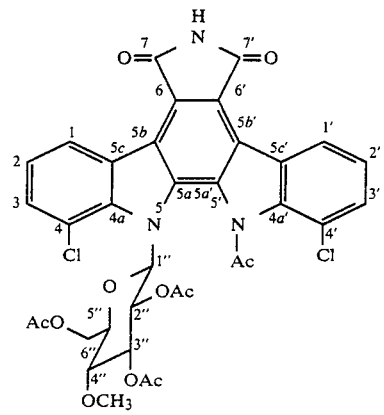

II wherein Ac represents

3. The compound 5'-N-methylrebeccamycin having the formula

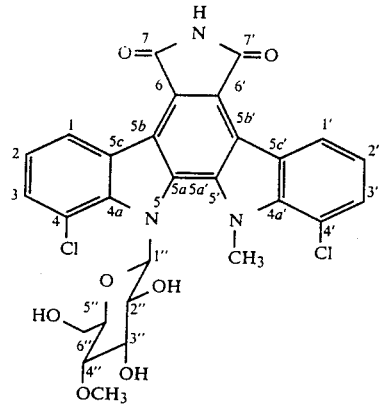

* * * * *